US005401626A

United States Patent [19]

Kondo et al.

[11] Patent Number: 5,401,626

[45] Date of Patent: Mar. 28, 1995

[54] CDNA FRAGMENT OF THE GENE FOR THE HEMAGGLUTININ NEURAMINIDASE OF HUMAN PARAINFLUENZA TYPE 2 VIRUS AND MATERIALS CONTAINING THE CDNA FRAGMENT

[75] Inventors: Kunio Kondo, Ushiku; Mitsuo Kawano; Yasuhiko Ito, both of Tsu, all of Japan

[73] Assignee: Fujikura Kasei Co., Ltd., Tokyo, Japan

[21] Appl. No.: 801,165

[22] Filed: Nov. 27, 1991

Related U.S. Application Data

[63] Continuation-in-part of Ser. No. 539,613, Jun. 18, 1990, abandoned.

[30] Foreign Application Priority Data

Jun. 18, 1989 [JP] Japan .................................. 1-154746

[51] Int. Cl.[6] .................................... C12Q 7/70

[52] U.S. Cl. .................................... 435/5; 435/6; 536/24.1; 536/24.32; 436/63

[58] Field of Search ...................... 435/5, 6, 91, 172.3, 435/69.1, 810; 436/63; 536/27, 23.72, 24.1, 24.32; 935/2, 19, 77, 78

U.S. PATENT DOCUMENTS 4,355,102 10/1982 Quash

FOREIGN PATENT DOCUMENTS

GB2,161,814 1/1986 UK

EP0,015,841 9/1980 Europe

OTHER PUBLICATION

WORLD PATENTS INDEX LATEST, AN 88-210707, Derwent Publications, Ltd., London, GB, Week 8830 of JP63148987, June 1988.

Landry et al, "Nucleic Acid Hybridization in the Diagnosis of Viral Infections", CLINICS IN LABORATORY MEDICINE, Vol. 5, No. 3, Sept. 1985, pgs. 513–529, US.

Kovamees et al, "Complete Nucleotide Sequence of the Hemagglutinin-Neuraminidase (HN) mRNA of mumps virus and comparison of Paramyxovirus HN Proteins", VIRUS RESEARCH, Vol. 12, No. 1, 1988, Pages 87–96, Amsterdam, NL.

Kawano et al, "Sequence determination of the hemagglutinin-neuraminidase (HN) gene of human parainfluenza type 2 virus. . .", VIROLOGY, Vol. 174, Jan. 1990, pages 308–313, New York, US.

Precious et al, "Sequence of analysis of the HN gene of parainfluenza virus type 2", THE JOURNAL OF GENERAL VIROLOGY, Vol. 71, No. 5, May 1990, pgs. 1163–1168, Reading, GB.

*Primary Examiner*—Christine M. Nucker

*Assistant Examiner*—Laurie Scheiner

*Attorney, Agent, or Firm*—Frishauf, Holtz, Goodman & Woodward

[57] ABSTRACT

A fragment of the gene for the hemagglutinin neuraminidase (HN protein) of human parainfluenza Type 2 virus (PIV-2) and materials containing such fragment. The fragment is complementary to the gene RNA for the PIV-2 HN protein and contains the entire coding regions for the PIV-2 HN protein. The fragment is useful as a test agent or a therapeutic agent for PIV-2 infections.

7 Claims, 1 Drawing Sheet

CDNA FRAGMENT OF THE GENE FOR THE HEMAGGLUTININ NEURAMINIDASE OF HUMAN PARAINFLUENZA TYPE 2 VIRUS AND MATERIALS CONTAINING THE CDNA FRAGMENT

This application is a continuation-in-part application of application Ser. No. 07/539,613, filed Jun. 18, 1990, now abandoned.

BACKGROUND OF THE INVENTION

1. Field of the Invention

This invention relates to the gene and a new fragment of the gene for the hemagglutinin neuraminidase (called the "HN" protein for short hereinbelow) of human parainfluenza Type 2 virus (called "PIV-2" for short hereinbelow) and materials containing said gene or fragment. More particularly, the present invention is concerned with a gene or fragment thereof which is complementary to the gene RNA for the PIV-2 HN protein and, furthermore, contains the entire coding areas for PIV-2 HN protein. The gene or fragment being useful as a test agent or a therapeutic agent for PIV-2 infections.

2. Background Information

For enhancing the therapeutic effect on virus infections, it is necessary to identify the infectious virus and to conduct adequate therapy on the basis of such identification.

Viruses have heretofore been identified on the basis of serological properties. Methods for such identification include those known as the enzyme-linked immunosorbent assay (called "ELISA" for short hereinbelow), the neutralization reaction, the complement fixation reaction, the hemagglutination inhibition reaction, the fluorescent antibody technique and the agar precipitation reaction. All of these involve an assay of the antibody to a given virus in the test material. In order to make an accurate determination the assay must be run at a stage at which the antibody titer for the virus begins to increase, generally a week after infection and, in some cases, a re-assay after several weeks is required. It is therefore a problem that diagnosis prior to onset of the symptoms caused by the infection or early diagnosis is hardly feasible.

For the determination of PIV-2 an ELISA is usually employed by which an antibody against PIV-2 in a test specimen is assayed, for example, by adding a test specimen to a plate on which PIV-2 has been fixed, allowing a reaction to proceed, washing the plate, further adding antiPIV 2 antibody to the plate, allowing a reaction to proceed, then adding the enzyme-labelled antibody to the reaction mixture, allowing a reaction to proceed and the problem as mentioned above, that is, a difficulty in presymptom and early diagnoses with a result that initiation of the treatment is necessarily delayed, so that enhancement of the therapeutic effect is difficult.

The present invention solves such problems and particularly provides a gene or a fragment of the gene useful in test agents, which make early diagnosis of PIV-2 infections possible.

SUMMARY OF THE INVENTION

This invention is an approach to solve the problem of difficulty in diagnosis of PIV-2 infections prior to the onset or at the early stages of the infection by providing a fragment of the gene for the HN protein of PIV-2 (occasionally called "DNA fragment" for short hereinbelow) which comprises a unit of all or at least 14 consecutive bases of the following base sequence (I) (SEQ ID NO:1):

```
11
GCACGAACCC  TTAAGGTGTC  GTAACGTCTC  GTGACACCGG  GTTCAGTTCA  AATATCGACC
TCTAACCCAA  TTTAACACCC  ATTCTTATAT  AAGAACACAG  TATAATTTAA  TCACAAAAGA
CCTCAAAAAC  TGACACAGCT  TGATCCACTC  AACATATAAT  TGTAAGATTA  ATAATAATGG
AAGATTACAG  CAATCTATCT  CTTAAATCAA  TTCCTAAAAG  GACATGTAGA  ATCATTTTCC
GAACTGCCAC  AATTCTTGGA  ATATGCACAT  TGATTGTTCT  ATGTTCAAGT  ATTCTTCATG
AGATAATTCA  TCTTGATGTT  TCCTCTGGTC  TCATGGATTC  CGATGATTCA  CAGCAAGGCA
     376
TTATTC
```

The DNA fragment provided by the invention has complementation to the gene RNA of the PIV-2 HN protein and therefore, when used in test agents for the identification of PIV-2, direct identification of PIV-2 can be attained and the problems associated with prior art indirect identification methods using the antibody assay can be solved. The DNA fragment of the invention is also useful in therapeutic uses for PIV-2 infections because it contains the entire coding areas for the PIV-2 HN protein and so the expressed HN protein can be used as an antigen for the preparation of antibodies or as a starting material for vaccines.

The gene for the hemagglutinin neuraminidase of human parainfluenza Type 2 virus has a following base sequence (II) (SEQ ID NO:2):

```
CCTAAAATAA  GCACGAACCC  TTAAGGTGTC  GTAACGTCTC  GTGACACCGG  GTTCAGTTCA   60
AATATCGACC  TCTAACCCAA  TTTAACACCC  ATTCTTATAT  AAGAACACAG  TATAATTTAA  120
TCACAAAAGA  CCTCAAAAAC  TGACACAGCT  TGATCCACTC  AACATATAAT  TGTAAGATTA  180
ATAATAATGG  AAGATTACAG  CAATCTATCT  CTTAAATCAA  TTCCTAAAAG  GACATGTAGA  240
ATCATTTTCC  GAACTGCCAC  AATTCTTGGA  ATATGCACAT  TGATTGTTCT  ATGTTCAAGT  300
ATTCTTCATG  AGATAATTCA  TCTTGATGTT  TCCTCTGGTC  TCATGGATTC  CGATGATTCA  360
CAGCAAGGCA  TTATTCAGCC  TATTATAGAA  TCATTAAAAT  CATTAATTGC  TTTGGCTAAC  420
CAGATTCTGT  ACAATGTTGC  AATAATAATT  CCTCTTAAAA  TTGACAGTAT  CGAGACTGTA  480
ATATTCTCTG  CTTTAAAGGA  TATGCATACT  GGGAGCATGT  CCAACACCAA  CTGTACACCC  540
GGAAATCTGC  TTCTGCATGA  TGCAGCGTAC  ATCAATGGAA  TAAACAAATT  CCTTGTACTT  600
AAATCATACA  ATGGGACGCC  TAAATATGGA  CCTCTCCTAA  ATATTCCCAG  CTTTATCCCC  660
TCAGCAACAT  CTCCCAACGG  GTGCACTAGA  ATACCATCAT  TTTCACTCAT  TAAGACCCAT  720
TGGTGTTACA  CTCACAATGT  AATGCTTGGA  GATTGCCTCG  ATTTCACGAC  ATCTAATCAG  780
TATTTAGCAA  TGGGGATAAT  ACAACAATCT  GCTGCAGCAT  TTCCAATCTT  CAGGACTATG  840
AAAACCATTT  ACCTAAGTGA  TGGAATCAAT  CGCAAAAGCT  GTTCAGTCAC  TGCTATACCA  900
GGAGGTTGTG  TCTTGTATTG  CTATGTAGCT  ACAAGATCTG  AGAAAGAAGA  TTATGCCACA  960
```

-continued

```
ACTGATCTAG  CTGAACTGAG  ACTTGCTTTC  TATTATTATA  ATGATACCTT  TATTGAAAGA  1020
GTCATATCTC  TTCCAAATAC  AACAGGGCAA  TGGGCCACAA  TCAATCCTGC  AGTTGGAAGC  1080
GGGATCTATC  ATCTAGGCTT  TATCTTATTT  CCTGTATATG  GTGGTCTCAT  AAGTGGGACT  1140
CCTTCCTACA  ACAAGCAGTC  CTCACGCTAT  TTTATCCCAA  AACATCCCAA  CATAACCTGT  1200
GCCGGTAACT  CCAGCGAACA  GGCTGCAGCA  GCACGGAGTT  CCTATGTAAT  CCGTTATCAC  1260
TCAAACAGGT  TGATTCAGAG  TGCTGTTCTT  ATTTGCCCAT  TGTCTGACAT  GCACACAGCA  1320
AGGTGTAATC  TAGTTATGTT  TAACAATTCT  CAAGTCATGA  TGGGTGCAGA  AGGTAGGCTC  1380
TATGTTATTG  ACAATAATTT  GTATTATTAT  CAACGTAGTT  CCTCTTGGTG  GTCTGCATCG  1440
CTTTTTTACA  GGATCAATAC  AGATTTTTCT  AAAGGAATTC  CTCCTATCAT  TGAGGCTCAA  1500
TGGGTACCGT  CCTATCAAGT  TCCCCGTCCT  GGAGTCATGC  CATGCAATGC  AACAAGTTTT  1560
TGCCCTGCTA  ATTGCATCAC  AGGGGTGTAC  GCAGATGTGT  GGCCGCTTAA  CGATCCAGAA  1620
CCCACATCAC  AAAATGCTCT  GAATCCCAAC  TATCGATTTG  CTGGAGCCTT  TCTCAGAAAT  1680
GAGTCCAACC  GAACCAATCC  CACATTCTAC  ACTGCATCAG  CCAGCGCCCT  ACTAAATACT  1740
ACCGGATTCA  ACAACACCAA  TCACAAAGCA  GCATATACGT  CTTCAACCTG  CTTTAAGAAT  1800
ACTGGAACTC  AAAAGATTTA  TTGTTTGATA  ATAATTGAAA  TGGGCTCATC  TCTTTTAGGG  1860
GAGTTCCAAA  TAATACCATT  TCTAAGGGAA  CTAATACCTT  AATACTATTG  AATGAAGACT  1920
CCAGATTCAA  TAATAATTGA  AAGGCTCTCT  ATCTTATGCA  ATAGTTATAC  GTTTTGGCTG  1980
TATTAGAATG  TTATAGATTC  TGCTGTTTTT  CCCATATGAA  GCAATCCTTC  AACACCGACT  2040
TAGGTTCAAT  TTTCTCATCA  TTTACTGTTG  TAATTCAATC  TTACTAAAGT  TATTCCGATA  2100
TTTAAGAAAA  AA                                                          2112
```

DETAILED DESCRIPTION OF THE INVENTION

Figure 1:
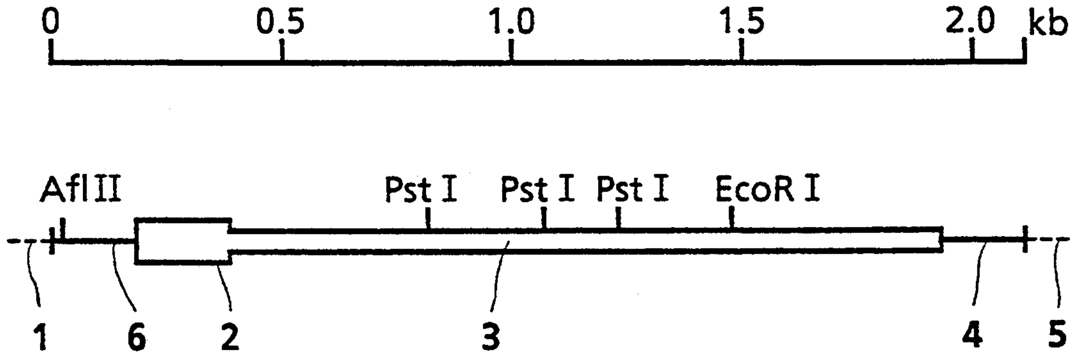
FIG. 1 is a restriction enzyme map of the cDNA region of DNA (pM2H) represented by the above-mentioned formula exhibiting complementation to the PIV-2 HN protein gene.

The DNA fragment (and gene) of the invention represented by the above-mentioned sequences can be prepared by conventional processes without particular limitation, which include, for example, (a) introducing cDNA prepared from mRNA of PIV-2-infected cells into an appropriate vector such as a plasmid vector of *Escherichia coli*, cloning of the cDNA in *E. coli*, isolating the clone coding for a gene for the PIV-2 HN protein, for example, by (1) screening using nucleocapsid RNA as a probe, or (2) screening using an oligonucleotide synthesized on the basis of the base sequence represented by the abovementioned formula as a probe, or (3) screening using antibodies against PIV-2, and separating the insert DNA from plasmid of the isolated clone, (b) preparing the synthetic nucleotide according to the phosphamidide method (*Nature*, vol. 310, Page 105, 1984) on the basis of the base sequences represented by the abovementioned formulas which are complementary to the gene RNA of the PIV-2 HN protein, or (c) combining (a) and (b) above.

The DNA fragment (and gene) of the invention produced by the above-described processes can be used in the following ways:

For example, the identification of PIV-2 is accomplished by the Northern hybridization (called the "Northern method" for short hereinbelow) in which the DNA fragment obtained as above, after further cutting into fragments of at least 14 consecutive bases, preferably 17 or more consecutive bases, more preferably 20 or more consecutive bases with appropriate restriction enzymes (such as PstI and EcoRI) if required, is labelled, for example, with a radioisotope for use as a test agent. The test agent is reacted with a nylon membrane or the like on which the RNA extracted from a test specimen (such as laryngeal fluid) is fixed and then a determination is made by autoradiography or other techniques.

In the present invention, whereas the unit of all or at least 14 bases of the above-mentioned formula (I) per se is useful as a test agent, said unit may also be incorporated into an appropriate DNA vector for use as above. In addition, said vector may not necessarily be a DNA vector, but may be used in the form of a material incorporated into or admixed with another appropriate material such as a polymer, cellulose, glass, ceramic or a pharmaceutical.

EXAMPLES

The invention will be described in more detail in the following examples.

Application to Test Agents

(1) Preparation of RNA

Vero cells were grown in Eagle's essential medium containing 5% fetal calf serum, and the medium was then replaced by freshly prepared Eagle's essential medium containing actinomycin D (2 μg/ml), which was then inoculated with PIV-2 (Toshiba strain). Cultivation was made in the same medium for 24 hours. The virus-infected culture cells were stripped off with a trypsin/EDTA mixture and then collected by centrifugation at 8000 rpm for 10 minutes. To the cells was added a guanidine isothiocyanate solution (6M guanidine isothiocyanate, 5 mM sodium citrate, 0.1M 2-mercaptoethanol and 0.5% sodium lauroylsarcosinate), and the mixture was quickly treated in a homogenizer to give a solution. The chromosome DNA was sheared by passing the solution five times through a 21-gauge needle attached to a syringe. The cytolysate thus obtained was centrifuged again at 8000 rpm. 9 ml of the supernatant was layered onto 3 ml of a 5.7M cesium chloride solution placed in a separate centrifugal tube, which was ultracentrifuged in a Beckman rotor (Beckman SW40Ti rotor) at 18° C. at 37000 rpm for 18 hours. After centrifugation, an RNA pellet was recovered.

From the RNA thus obtained was separated and purified polyadenylated mRNA (called "poly(A+)-RNA" for short hereinbelow) using oligo dT cellulose Type 7 (manufactured by Pharmacia).

(2) Preparation of a cDNA Library

A cDNA library was synthesized according to the method of Okayama-Berg. To 4 μg of the poly(A+)-RNA prepared above was added 5 μl of distilled water. The mixture was heated at 65° C. for 10 minutes followed by rapid cooling. Then, 10 μl of oligo dT-primed vector (oligo dT was added to KpnI site of pUCl18 vector (0.8–1.2 μg/μl)), 3 μl of a solution for synthetic reaction (500 mM tris-hydrochloric acid buffer of pH 8.3, 300 mM potassium chloride, 80 mM magnesium chloride and 3 mM dithiothreitol) and 1 μl each of 20 mM dATP, 20 mM dCTP, 20 mM dGTP and 20 mM dTTP were added.

Further added were 20 units of RNasin and 40 units of reverse transcriptase and then distilled water to make up the entire volume to 30 μl. The reaction was made at 42° C. for 30 minutes to synthesize first-strand cDNA. After completion of the synthesizing the first-strand cDNA, 10–30 dG bases were added using a terminal deoxynucleotidyl transferase in the presence of dGTP. Then, digestion was made with a HindIII restriction enzyme, and annealing was made with a linker having a dC base chain followed by ring closure with *E. coli* ligase. Finally, the second strand was synthesized with a DNA polymerase in the presence of RNaseH thereby preparing a perfect plasmid DNA. To 100–200 μl of competent cells (DH 1) obtained by a calcium chloride treatment were then added 10 μl of a mixed solution of a 0.4M magnesium chloride and 0.1M calcium chloride and 0.02 g of the DNA as prepared above, and the mixture was allowed to stand at 0° C. for 40 minutes and then at 42° C. for 90 seconds followed by addition of 1.5 ml of a medium (a solution of 10 g of bactotrypton, 5 g of yeast extract and 5 g of sodium chloride in 1000 ml of distilled water). Allowing the mixture to stand at 37° C. for 40 minutes yielded the transformed cells.

Thus, there were obtained 1400 independent clones in the presence of ampicillin by introducing 0.02 μg of the plasmid DNA into 200 μl of the competent cells (DH 1).

(3) Preparation of a Nucleocapsid RNA Probe

To PIV-2 infected vero cells was added a solution (0.15M sodium chloride, 0.05M tris-hydrochloric acid buffer) containing 0.6% Nonidet P-40 and 10 mM vanadium ribonucleotide complex. The mixture was solubilized by pipetting in ice for one hour and centrifuged at 8000 rpm for 10 minutes. Onto 1 ml of a 40%, 2.5 ml of a 30% and 1 ml of a 25% aqueous solutions of cesium chloride layered in this order in a centrifugal tube was further layered 9 ml of the supernatant obtained above by centrifugation, and the layered solutions were subjected to equilibrium density-gradient centrifugation in a Beckman rotor SW40Ti at 37000 rpm for 18 hours at 16° C. There was recovered a virus nucleocapsid band formed in the layer of 30% aqueous cesium chloride solution, which was then subjected to proteolysis with 0.1% SDS and proteinase K (2.5 mg/ml) at 56° C. for 15 minutes. Subsequent treatments with phenol and a phenol/chloroform mixture produced a nucleocapsid RNA. To the nucleocapsid RNA thus produced was added a 50 mM trishydrochloric acid buffer of pH 9.7, and the mixture was heated at 95° C. for 10 minutes followed by cooling slowly to room temperature. To 20 μl of the RNA solution were added 10 μl of a buffer (250 mM tris-hydrochloric acid, 50 mM magnesium chloride, 25 mM DTT, 7.5 mM spermine and 500 mM potassium chloride), 3 μl of $^{32}P$ ATP (100 μCi/600 pM) and 2 units of $T_4$-DNA kinase, and the mixture was diluted with distilled water to a total volume of 50 μ. The resulting mass was allowed to react at 37° C. for one hour to give a nucleocapsid RNA probe.

(4) Colony Hybridization

100–200 μl of the transformed cells prepared above were seeded onto agar plates each 15 cm in diameter (10 g of bactotrypton, 5 g of yeast extract, 5 g of sodium chloride and 15 g of agar added and diluted with distilled water to a total volume of 1000 ml) containing ampicillin (120 μg/ml) and incubated at 37° C. for 12 hours. The formed colonies were transferred to nitrocellulose membranes, which were incubated at 37° C. for 6 hours on fresh agar plate. The membranes were then treated with a 0.5N sodium hydroxide/1.5M sodium chloride mixture for 10 minutes and further with a 0.5M tris-hydrochloric acid buffer of pH 8.0 for 10 minutes and subsequently rinsed with a mixed solution containing a 0.3M sodium chloride/0.03M sodium citrate for 5 minutes. After rinsing, the membranes were air dried and suction baked at 80° C. for one hour to fix the DNA on the membranes.

To the membrane thus prepared was added a prehybridization solution composed of 1 ml of denatured salmon RNA (1 mg/ml), 7.5 ml of SSPE solution (3.6M sodium chloride, 200 mM sodium dihydrogen phosphate and 20 mM EDTA), 1.25 ml of Denhardt's solution (2% BSA, 2% Ficoll and 2% polyvinylpyrrolidone) and 1.25 ml of 10% SDS per 5 membranes followed by reaction at 42° C. for 12 hours. Then, the nucleocapsid RNA probe mentioned above was added to a fresh prehybridization solution prepared as above at a level of 5,000,000 Ci/ml followed by reaction at 42° C. for 18 hours. After completion of the reaction, the membranes were washed twice in a 1:20-diluted SSPE solution containing 0.1% SDS at 42° C. for 5 minutes and then twice in a 1:200-diluted SSPE solution containing 0.1% SDS at 42° C. for 15 minutes. After completion of the washing, the membrane was air dried and subjected to autoradiography using X-ray film (RX5, manufactured by Kodak) at −80° C. for 12 hours. There were obtained several positive clones.

(5) Northern Method

The Northern method was employed for the positive clones obtained above. Electrophoresis was conducted in 1.5% agarose gel respectively of the PIV-2-infected cell-derived poly(A+)RNA produced by the procedures under (1) above, a virus-noninfected cell-derived poly(A+)RNA and an rRNA marker. After electrophoresis was completed, the RNA was transferred from agarose gel to a nylon membrane (Hybond-N, manufactured by Amersham, Inc.) which was air dried and UV irradiated to produce a covalent bond of the RNA with the nylon membrane. Hybridization was then carried out using the above-obtained positive clones respectively as a probe.

Thus, the nylon membrane was allowed to react in the abovementioned prehybridization solution at 42° C. for 12 hours. To the prehybridization solution was added a $^{32}P$-labelled probe prepared from each of the positive clones at a level of 1,000,000 Ci/ml followed by reaction at 42° C. for 18 hours. After completion of the reaction, washing were made in the same way as under (4) above, and autoradiography was made using X-ray film. There was then obtained one clone that hybridizes at a site corresponding to the base 2100, which was named pM2H.

It is noted that the probe for each of the positive clones was obtained by digesting each clone with HindIII and EcoRI, then separating inserted DNA by electrophoresis using low melting agarose, extracting it and subjecting it to random prime labelling using $^{32}P$ dCTP.

(6) Preparation of a Restriction Map of the DNA Exhibiting Complementation to the PIV-2 HN Protein Gene and Determination of the Base Sequence The clone pM2H obtained above under (5) was cleaved with various restriction enzymes to prepare its restriction map. The results are shown in FIG. 1.

FIG. 1 shows a restriction enzyme map prepared as follows:

Fragments produced by cleaving the clone pM2H with each of the restriction enzymes AflII, PstI and EcoRI were respectively introduced into multicloning sites of the plasmid pUCll8 and sequenced using Sequence TM kit (manufactured by TOYOBO CO., LTD.); deletion mutants were also prepared and sequenced using a deletion kit for kilo sequencing (manufactured by Takara Shuzo Co., Ltd.) to determine the base sequence. In the figure, 1 and 5 indicate the vector DNA, 4 and 6 the non-coding region and 2 and 3 the coding region. Among them, 2 and 6 represent the DNA fragment exhibiting complementation to PIV-2 HN protein gene RNA.

The results are as shown by the above-mentioned formula II.

(7) Identification of PIV-2

(7-1) In the case using a DNA fragment represented by the sequence of from base 1 to base 502 of the above formula A probe was prepared by cleaving the clone pM2H obtained above under (5) with EcoT22I and HindIII followed by electrophoresis using low melting agarose to separate a portion of the inserted DNA, extracting it and subjecting it to random prime labelling using $^{32}P$. Then, 0.35 $\mu g$ each of the PIV-2-infected cell-derived RNA obtained by the procedures under (1) above and the virus-noninfected cell-derived RNA was blotted on a nylon membrane, which was air dried, UV irradiated and subjected to reactions and radioautography in exactly the same way as in the Northern method described above under (5). As a result, there was observed positive reaction formed with said probe which has formed a hybrid with RNA for the PIV-2 gene in the specimen in the area blotted with the PIV-2-infected cell-derived RNA thereby demonstrating the infection with PIV-2. On the contrary, there was observed no reaction at all in the area blotted with the virus-noninfected cell-derived RNA.

(7-2) In the case using the whole of an insert DNA represented by the sequence of from base 1 to base 2112 of the above formula The clone pM2H was cleaved with HindIII and SacI followed by electrophoresis on low-melting agarose. A band electrophoretically moved to a position corresponding to ca. 2100 base pairs was excised, extracted and precipitated with ethanol to recover an insert DNA. To the insert DNA were added 2 $\mu l$ of a buffer solution (0.5M tris-hydrochloric acid pH 7.6, 0.1M $MgCl_2$, 50 mM dithiothreitol, 1 mM spermidine hydrochloride and 1 mM EDTA), 11.4 $\mu l$ of distilled water, 5 $\mu l$ of ($\gamma^{32}P$)ATP (2 nmoles/$\mu l$) and 8 units of bacteriophage T4 polynucleotide kinase per $\mu l$ of the DNA (10 pmoles/$\mu l$) followed by reaction at 37° C. for 45 minutes. The reaction solution was then purified with Biogel P60 (Nihon Bio-rad Laboratories K. K.), and the purified product thus obtained was used as probe.

A nylon membrane was blotted with 0.35 $\mu g$ each of the PIV-2-infected cell-derived RNA and the virus-noninfected cell-derived RNA, respectively produced by procedures described under (1) above, then air dried, UV irradiated and allowed to react in a prehybridization solution as mentioned under (5) above at 42° C. for 18 hours. Subsequently, the above-prepared probe which had been kept on a boiling-water bath for 2 minutes and then rapidly cooled was added so as to give a radioactivity of 1,000,000 Ci/ml. The resulting mixture was reacted at 42° C. for additional 18 hours. After completion of the reaction, the reaction mixture was washed twice with a 1:20-diluted SSPE solution containing 0.1% SDS at 42° C. for 5 minutes and then twice with a 1:200-diluted SSPE solution containing 0.1% SDS at 42° C. for 15 minutes. After completion of the washing the membrane was air dried and subjected to autoradiography with an X-ray film at −80° C. for 12 hours.

There was thus observed a positive reaction in the area blotted with the PIV-2-infected cell-derived RNA. The reaction was one which occurred with the probe that had formed a hybrid with the PIV-2 virus RNA in the sample so that it demonstrated the infection with PIV-2. On the contrary, there was observed no reaction at all in the area blotted with the virus-noninfected cell-derived RNA.

(7-3) In the case using a fragment containing the sequence of from base 147 to base 232 in the base sequence represented by the above formula The clone pM2H was cleaved with AluI and AflIII followed by electrophoresis on low-melting agarose. A band electrophoretically moved to a position corresponding to ca. 85 base pairs was excised, and a DNA fragment extracted and recovered by precipitation with ethanol. The DNA fragment thus obtained was at random labeled for use as probe. Thus, to 0.1 $\mu g$ of the DNA fragment was added 10 $\mu$of distilled water, and to the mixture kept in boiling water for 2 minutes and then rapidly cooled were added 1 $\mu l$ of bovine albumin (10 mg/ml), 11.4 $\mu l$ of a Random solution (0.44M HEPES pH 6.6, 110 mM tris-hydrochloric acid pH 8, 11 mM $MgCl_2$, 2 mM 2-mercaptoethanol, 44 $\mu M$ dATP, 44 $\mu M$ dGTP, 44 $\mu M$ dTTP, 0.12 mn tris-hydrochloric acid pH 7.5, 0.12 mM EDTA and 11 units/ml oligonucleotide pd(N)$_6$ (Pharmacia AB)) and 2.5 units of klenow followed by reaction at room temperature for 6 hours. The reaction solution thus obtained was purified with Bio-gel P60 for use as probe.

Then, a nylon membrane was blotted with 0.35 $\mu g$ each of the PIV-2-infected cell-derived RNA and the virus-noninfected cell-derived RNA, respectively produced by the procedures described under (1) above, then air dried, UV irradiated and allowed to react in a prehybridization solution as mentioned under (5) above at 42° C. for 18 hours. Subsequently, the above-prepared probe which had been kept on a boiling-water bath for 2 minutes and then rapidly cooled was added so as to give a radioactivity of 1,000,000 Ci/ml. The resulting mixture was reacted at 42° C. for additional 18 hours. After completion of the reaction, the reaction mixture was washed twice with a 1:20-diluted SSPE solution containing 0.1% SDS at 42° C. for 5 minutes and then twice with a 1:200-diluted SSPE solution containing 0.1% SDS at 42° C. for 15 minutes. After completion of the washing the membrane was air dried and subjected to autoradiography with an X-ray film at −80° C. for 12 hours.

There was thus observed a positive reaction in the area blotted with the PIV-2-infected cell-derived RNA. The reaction was one which occurred with the probe that had formed a hybrid with the PIV-2 virus RNA in the sample so that it demonstrated the infection with PIV-2. On the contrary, there was observed no reaction at all in the area blotted with the virus-noninfected cell-derived RNA.

(7-4) In the case using an oligonucleotide synthesized on the bases of the sequence of from base 168 to base 186 in the base sequence represented by the abovementioned formula Oligonucleotides with ten-odd or more bases can be synthesized on the basis of the base sequence represented by the above-mentioned formula and used as probe.

An oligonucleotide (5'-AATTGTAAGATTAATAATA-3') was synthesized using a DNA synthesizer, Model 381A DNA synthesizer (Applied Biosystems Japan K. K.) and purified using an oligonucleotide purification cartridge (Applied Biosystems Japan K. K.). To the oligonucleotide thus obtained were added 2 μl of the same buffer solution as under (7-2) above, 11.4 μl of distilled water, 5 μl of ($\gamma^{32}$P)ATP (2 nmoles/μl) and 8 units of bacteriophage T4 polynucleotide kinase per μl of the oligonucleotide (10 pmoles/μl) followed by reaction at 37° C. for 45 minutes. The reaction solution was purified with Bio-gel P60, and the purified product was used as probe.

Then, a nylon membrane was blotted with 0.35 μg each of the PIV-2-infected cell-derived RNA and the virus-noninfected cell-derived RNA, respectively produced by the procedures described under (1) above, then air dried, UV irradiated and reacted in a prehybridization solution as mentioned under (5) above at 42° C. for 12 hours. Subsequently, the above-prepared probe was added so as to give a radioactivity of 1,000,000 Ci/ml followed by reaction at 42° C. for additional 18 hours. After completion of the reaction, the reaction mixture was washed twice with a 1:20-diluted SSPE solution containing 0.1% SDS at 42° C. for 5 minutes and then twice with a 1:200-diluted SSPE solution containing 0.1% SDS at 42° C. for 15 minutes. After completion of the washing the membrane was air dried and subjected to autoradiography with an X-ray film at −80° C. for 12 hours.

There was thus observed a positive reaction in the area blotted with the PIV-2-infected cell-derived RNA. The reaction was one which occurred with the probe that had formed a hybrid with the PIV-2 virus RNA in the sample so that it demonstrated the infection with PIV-2. On the contrary, there was observed no reaction at all in the area blotted with the virus-noninfected cell-derived RNA.

Application to Therapeutic Drugs

In the case where protein encoded in the clone pM2H is expressed:

The clone pM2H contains almost the entire area of the gene for HN protein and all of the area coding for HN protein so that incorporation of insert DNA of the clone pM2H into an appropriate vector would enable expression of protein encoded in the gene. The expressed protein can be employed, for example, as an antigen for producing antibodies or a starting material for the preparation of vaccines. For the expression of protein can be used various methods using, for example, an in vitro synthesis system with a rabbit erythrocyte lysate, a system with a microorganism such as *Escherichia coli* or *Bacillus subtilis,* or a system with cells of yeast, an insect or a mammal to express protein encoded in various genes.

An insert DNA with such deletion that the initiation codon of the insert DNA of the clone pM2H (ATG, base 187—base 189 of the base sequence represented by the above-mentioned formula) will be in 10–15 base pairs from the libosome bonding site of the expression vector pKK223-3 (manufactured by Pharmacia). The deletion-insert DNA is introduced into EcoRI or SmaI site of the vector pKK223-3 with direction adjusted.

The clone thus obtained is introduced into *E. coli* JM109, and the *E. coli* is incubated in YT culture medium (16 g of bactotrypton, 10 g of yeast extract and 5 g of sodium chloride is dissolved in distilled water to a volume of 1 lit.) containing 100 μg/ml of ampicillin with stirring at 37° C. for 12 hours. Isopropylthiogalactoside is then added to a concentration of 2 mM, and incubation continued with stirring at 37° C. for additional 5 hours. After completion of the incubation, the culture is subjected to centrifugal separation at 10000 rpm at 15° C. for 10 minutes. The precipitates thus obtained is washed with 30 mM tris-hydrochloric acid buffer (pH 7.5) containing 30 mM sodium chloride and then suspended in the above-mentioned buffer. To the suspension are added 1 mg of lysozyme and 25 μl of 0.25M EDTA per ml of the suspension, and the mixture allowed to stand at room temperature for 15 minutes. Then, freezing and melting are repeated four times. The molten mass is then centrifuged at 10000 rpm at 4° C. for 60 minutes, and the supernatant isolated. The protein in the supernatant is identified according to the methods of Komada et al. (*J. Gen. Virol.,* 1989, Vol. 70, pp. 3487–3492) and of Itoh et al. (*Archives of Virology,* 1987, Vol. 95, pp. 211–224). Thus, analysis was conducted by immunoprecipitation procedures using antiPIV-2 antibodies followed by polyacrylamide gel electrophoresis to confirm that the HN protein is expressed in *E. coli.*

Effect of the Invention

The DNA fragment provided by the present invention exhibits complementation specifically to RNA for the PIV-2 HN protein gene and can be used as a test agent for the early diagnosis of PIV-2 infections. Furthermore, the DNA fragment of the invention is also useful in therapeutic uses for PIV-2 infections because it contains the entire coding areas for the PIV-2 HN protein so that the expressed HN protein can be used as an antigen for the preparation of antibodies or as a starting material for vaccines. It is therefore very useful in that concurrent application to both test and treatment of PIV-2 infections is feasible.

SEQUENCE LISTING ( 1 ) GENERAL INFORMATION:

( i i i ) NUMBER OF SEQUENCES: 2

-continued ( 2 ) INFORMATION FOR SEQ ID NO: 1:

( i ) SEQUENCE CHARACTERISTICS:
( A ) LENGTH: 366 base pairs
( B ) TYPE: nucleic acid
( C ) STRANDEDNESS: double
( D ) TOPOLOGY: linear ( i x ) FEATURE:
( D ) OTHER INFORMATION: The base sequences provided by the invention were determined by sequencing cDNA clone ( p M 2 H ). The cDNA clone, which was the double stranded and circular DNA, was synthesized from the gene RNA, which was single stranded and linear RNA, for the PIV-2 HN protein.

( x i ) SEQUENCE DESCRIPTION: SEQ ID NO: 1:

1 1

```
GCACGAACCC TTAAGGTGTC GTAACGTCTC GTGACACCGG GTTCAGTTCA AATATCGACC    70
TCTAACCCAA TTTAACACCC ATTCTTATAT AAGAACACAG TATAATTTAA TCACAAAAGA   130
CCTCAAAAAC TGACACAGCT TGATCCACTC AACATATAAT TGTAAGATTA ATAATAATGG   190
AAGATTACAG CAATCTATCT CTTAAATCAA TTCCTAAAAG GACATGTAGA ATCATTTTCC   250
GAACTGCCAC AATTCTTGGA ATATGCACAT TGATTGTTCT ATGTTCAAGT ATTCTTCATG   310
AGATAATTCA TCTTGATGTT TCCTCTGGTC TCATGGATTC CGATGATTCA CAGCAAGGCA   370
TTATTC                                                              376
```

( 2 ) INFORMATION FOR SEQ ID NO:2:

( i ) SEQUENCE CHARACTERISTICS:
( A ) LENGTH: 2112 base pairs
( B ) TYPE: nucleic acid
( C ) STRANDEDNESS: double
( D ) TOPOLOGY: linear ( i x ) FEATURE:
( D ) OTHER INFORMATION: The base sequences provided by the invention were determined by sequencing cDNA clone ( p M 2 H ). The cDNA clone, which was the double stranded and circular DNA, was synthesized from the gene RNA, which was single stranded and linear RNA, for the PIV-2 HN protein.

( x ) PUBLICATION INFORMATION:
( A ) AUTHORS: Kawano, Mitsuo, Bando, Hisanori, Yuasa, Tetsuya, Kondo, Kunio, Tsurudome, Masato, Komada, Hiroshi, Nishio, Machiko, Ito, Yasuhiko
( B ) TITLE: Sequence Determination of the Hemagglutinin-Neuraminadase (HN) Gene of Human Parainfluenza Type 2 Virus and the Construction of a Phylogenetic Tree for HN Proteins of All the Paramyxoviruses that Are Infectious to Humans
( C ) JOURNAL: Virology
( D ) VOLUME: 174
( E ) ISSUE:
( F ) PAGES: 308-313
( G ) DATE: 1990

( x i ) SEQUENCE DESCRIPTION: SEQ. ID NO:2:

```
CCTAAAATAA GCACGAACCC TTAAGGTGTC GTAACGTCTC GTGACACCGG GTTCAGTTCA    60
AATATCGACC TCTAACCCAA TTTAACACCC ATTCTTATAT AAGAACACAG TATAATTTAA   120
TCACAAAAGA CCTCAAAAAC TGACACAGCT TGATCCACTC AACATATAAT TGTAAGATTA   180
ATAATAATGG AAGATTACAG CAATCTATCT CTTAAATCAA TTCCTAAAAG GACATGTAGA   240
ATCATTTTCC GAACTGCCAC AATTCTTGGA ATATGCACAT TGATTGTTCT ATGTTCAAGT   300
ATTCTTCATG AGATAATTCA TCTTGATGTT TCCTCTGGTC TCATGGATTC CGATGATTCA   360
CAGCAAGGCA TTATTCAGCC TATTATAGAA TCATTAAAAT CATTAATTGC TTTGGCTAAC   420
```

-continued

CAGATTCTGT ACAATGTTGC AATAATAATT CCTCTTAAAA TTGACAGTAT CGAGACTGTA 480

ATATTCTCTG CTTTAAAGGA TATGCATACT GGGAGCATGT CCAACACCAA CTGTACACCC 540

GGAAATCTGC TTCTGCATGA TGCAGCGTAC ATCAATGGAA TAAACAAATT CCTTGTACTT 600

AAATCATACA ATGGGACGCC TAAATATGGA CCTCTCCTAA ATATTCCCAG CTTTATCCCC 660

TCAGCAACAT CTCCCAACGG GTGCACTAGA ATACCATCAT TTTCACTCAT TAAGACCCAT 720

TGGTGTTACA CTCACAATGT AATGCTTGGA GATTGCCTCG ATTTCACGAC ATCTAATCAG 780

TATTTAGCAA TGGGGATAAT ACAACAATCT GCTGCAGCAT TTCCAATCTT CAGGACTATG 840

AAAACCATTT ACCTAAGTGA TGGAATCAAT CGCAAAAGCT GTTCAGTCAC TGCTATACCA 900

GGAGGTTGTG TCTTGTATTG CTATGTAGCT ACAAGATCTG AGAAAGAAGA TTATGCCACA 960

ACTGATCTAG CTGAACTGAG ACTTGCTTTC TATTATTATA ATGATACCTT TATTGAAAGA 1020

GTCATATCTC TTCCAAATAC AACAGGGCAA TGGGCCACAA TCAATCCTGC AGTTGGAAGC 1080

GGGATCTATC ATCTAGGCTT TATCTTATTT CCTGTATATG GTGGTCTCAT AAGTGGGACT 1140

CCTTCCTACA ACAAGCAGTC CTCACGCTAT TTTATCCCAA AACATCCCAA CATAACCTGT 1200

GCCGGTAACT CCAGCGAACA GGCTGCAGCA GCACGGAGTT CCTATGTAAT CCGTTATCAC 1260

TCAAACAGGT TGATTCAGAG TGCTGTTCTT ATTTGCCCAT TGTCTGACAT GCACACAGCA 1320

AGGTGTAATC TAGTTATGTT TAACAATTCT CAAGTCATGA TGGGTGCAGA AGGTAGGCTC 1380

TATGTTATTG ACAATAATTT GTATTATTAT CAACGTAGTT CCTCTTGGTG GTCTGCATCG 1440

CTTTTTTACA GGATCAATAC AGATTTTTCT AAAGGAATTC CTCCTATCAT TGAGGCTCAA 1500

TGGGTACCGT CCTATCAAGT TCCCCGTCCT GGAGTCATGC CATGCAATGC AACAAGTTTT 1560

TGCCCTGCTA ATTGCATCAC AGGGGTGTAC GCAGATGTGT GGCCGCTTAA CGATCCAGAA 1620

CCCACATCAC AAAATGCTCT GAATCCCAAC TATCGATTTG CTGGAGCCTT TCTCAGAAAT 1680

GAGTCCAACC GAACCAATCC CACATTCTAC ACTGCATCAG CCAGCGCCCT ACTAAATACT 1740

ACCGGATTCA ACAACACCAA TCACAAAGCA GCATATACGT CTTCAACCTG CTTTAAGAAT 1800

ACTGGAACTC AAAAGATTTA TTGTTTGATA ATAATTGAAA TGGGCTCATC TCTTTTAGGG 1860

GAGTTCCAAA TAATACCATT TCTAAGGGAA CTAATACCTT AATACTATTG AATGAAGACT 1920

CCAGATTCAA TAATAATTGA AAGGCTCTCT ATCTTATGCA ATAGTTATAC GTTTTGGCTG 1980

TATTAGAATG TTATAGATTC TGCTGTTTTT CCCATATGAA GCAATCCTTC AACACCGACT 2040

TAGGTTCAAT TTTCTCATCA TTTACTGTTG TAATTCAATC TTACTAAAGT TATTCCGATA 2100

TTTAAGAAAA AA 2112

We claim:

1. A cDNA fragment of the gene for the hemagglutinin neuraminidase of human parainfluenza Type 2 virus consisting of a unit of all or at least 14 consecutive bases of the following base sequence (SEQ ID NO:1):

GCACGAACCC TTAAGGTGTC GTAACGTCTC

GTGACACCGG GTTCAGTTCA AATATCGACC

TCTAACCCAA TTTAACACCC ATTCTTATAT

AAGAACACAG TATAATTTAA TCACAAAAGA

CCTCAAAAAC TGACACAGCT TGATCCACTC

AACATATAAT TGTAAGATTA ATAATAATGG

AAGATTACAG CAATCTATCT CTTAAATCAA

TTCCTAAAAG GACATGTAGA ATCATTTTCC

-continued

GAACTGCCAC AATTCTTGGA ATATGCACAT

TGATTGTTCT ATGTTCAAGT ATTCTTCATG

AGATAATTCA TCTTGATGTT TCCTCTGGTC

TCATGGATTC CGATGATTCA CAGCAAGGCA

TTATTC.

2. The cDNA fragment of claim 1, which consists of 17 or more bases of SEQ ID NO:1.

3. The cDNA fragment according to claim 1, which consists of 20 or more bases of SEQ ID NO:1.

4. A method to detect a viral infection caused by human parainfluenza Type 2 virus which comprises labelling the cDNA fragment of claim 1 with a labelling substance to obtain a test agent, reacting the test agent with RNA extracted from a test specimen and assaying for the label.

5. The method according to claim 4, wherein the label is a radioisotope and the radioisotope is detected by an autoradiograph.

6. A composition comprising the fragment of claim 1 incorporated into a vector.

7. A cDNA fragment of the gene for the hemagglutinin neuraminidase of human parainfluenza Type 2 virus which consists of the following base sequence (SEQ ID NO:.1):

GCACGAACCC TTAAGGTGTC GTAACGTCTC

GTGACACCGG GTTCAGTTCA AATATCGACC

TCTAACCCAA TTTAACACCC ATTCTTATAT

-continued

AAGAACACAG TATAATTTAA TCACAAAAGA

CCTCAAAAAC TGACACAGCT TGATCCACTC

AACATATAAT TGTAAGATTA ATAATAATGG

AAGATTACAG CAATCTATCT CTTAAATCAA

TTCCTAAAAG GACATGTAGA ATCATTTTCC

GAACTGCCAC AATTCTTGGA ATATGCACAT

TGATTGTTCT ATGTTCAAGT ATTCTTCATG

AGATAATTCA TCTTGATGTT TCCTCTGGTC

TCATGGATTC CGATGATTCA CAGCAAGGCA

TTATTC.

* * * * *

UNITED STATES PATENT AND TRADEMARK OFFICE

CERTIFICATE OF CORRECTION

PATENT NO. : 5,401,626

DATED : Mar. 28, 1995

INVENTOR(S) : KONDO et al

It is certified that error appears in the above-indentified patent and that said Letters Patent is hereby corrected as shown below:

Title Page, Left Column, [30] Foreign Application Priority Data", delete "Jun. 18, 1989" and replace with --Jun. 19, 1989--.

Signed and Sealed this

Twenty-seventh Day of August, 1996

Attest:

BRUCE LEHMAN

*Attesting Officer*

*Commissioner of Patents and Trademarks*